United States Patent
Kim et al.

(10) Patent No.: US 9,474,503 B2
(45) Date of Patent: Oct. 25, 2016

(54) ULTRASOUND SYSTEM AND METHOD FOR DETECTING VECTOR INFORMATION USING TRANSMISSION DELAYS

(71) Applicant: SAMSUNG MEDISON CO., LTD., Gangwon-do (KR)

(72) Inventors: Deok Gon Kim, Seoul (KR); Min Woo Kim, Seoul (KR)

(73) Assignee: SAMSUNG MEDISON CO., LTD., Gangwon-Do (KR)

( * ) Notice: Subject to any disclaimer, the term of this patent is extended or adjusted under 35 U.S.C. 154(b) by 0 days.

(21) Appl. No.: 13/728,518

(22) Filed: Dec. 27, 2012

(65) Prior Publication Data
US 2013/0165777 A1  Jun. 27, 2013

(30) Foreign Application Priority Data
Dec. 27, 2011  (KR) .................. 10-2011-0143871

(51) Int. Cl.
A61B 8/00 (2006.01)
A61B 8/06 (2006.01)

(52) U.S. Cl.
CPC .................. A61B 8/06 (2013.01)

(58) Field of Classification Search
CPC ............ G10K 11/346; G01S 7/52085; G01S 15/8927; G01S 15/8997; A61B 8/06
USPC .................................. 600/437–469
See application file for complete search history.

(56) References Cited

U.S. PATENT DOCUMENTS

| | | | |
|---|---|---|---|
| 4,182,173 A * | 1/1980 | Papadofrangakis et al. | 73/861.27 |
| 4,733,562 A * | 3/1988 | Saugeon | 73/626 |
| 5,291,892 A * | 3/1994 | O'Donnell | 600/454 |
| 5,443,071 A | 8/1995 | Banjanin et al. | |
| 5,568,813 A | 10/1996 | Deitrich et al. | |
| 5,865,751 A * | 2/1999 | Okuno et al. | 600/443 |
| 6,110,116 A | 8/2000 | Wright et al. | |
| 6,111,816 A * | 8/2000 | Chiang et al. | 367/7 |
| 6,148,224 A | 11/2000 | Jensen | |
| 6,363,033 B1 | 3/2002 | Cole et al. | |
| 2002/0012289 A1* | 1/2002 | Gilbert et al. | 367/135 |
| 2005/0018540 A1* | 1/2005 | Gilbert et al. | 367/138 |

(Continued)

FOREIGN PATENT DOCUMENTS

| | | |
|---|---|---|
| JP | 2006-055493 A | 3/2006 |
| JP | 2006-181361 A | 7/2006 |

(Continued)

OTHER PUBLICATIONS

Korean Office Action issued in Korean Application No. 10-2011-0143871 mailed May 15, 2013.

(Continued)

*Primary Examiner* — Sanjay Cattungal
(74) *Attorney, Agent, or Firm* — McDermott Will & Emery LLP (57) ABSTRACT

An ultrasound system and a method of detecting vector information with transmission delays are disclosed. In one embodiment, the ultrasound system includes: an ultrasound data acquisition unit configured to set at least two focal points and form ultrasound data corresponding to the respect two focal points by considering transmission delays to the respective focal points; and a processor configured to form vector information of a target object by using the ultrasound data.

2 Claims, 6 Drawing Sheets

(56) References Cited

U.S. PATENT DOCUMENTS

| | | | |
|---|---|---|---|
| 2005/0043622 A1* | 2/2005 | Jensen | 600/449 |
| 2005/0139006 A1* | 6/2005 | Lorraine et al. | 73/597 |
| 2006/0025687 A1* | 2/2006 | Kim et al. | 600/447 |
| 2012/0130248 A1* | 5/2012 | Fatemi | 600/454 |

FOREIGN PATENT DOCUMENTS

| | | |
|---|---|---|
| JP | 2007-075639 A | 3/2007 |
| KR | 10-2004-0069378 A | 8/2004 |

OTHER PUBLICATIONS

Korean Office Action issued in corresponding Korean Application No. 10-211-0143871, dated Jan. 23, 2014, with English translation.

Phillips P J et al:"Feasibility Study for a Two-Dimensional Diagnostic Ultrasound Velocity Mapping System", Ultrasound in Medicine and Biology, vol. 21, No. 2, Jan. 1, 1995, pp. 217-229.

Dunmire B et al:"Cross-Beam Vector Doppler Ultrasound for Angle-Independent Velocity Measurements", Ultrasound in Medicine and Biology, vol. 26, No. 8, Oct. 1, 2000, pp. 1213-1235.

Xu S et al:"Phased Array Pulse Doppler Tomography", Proceedings of the Ultrasonics Symposium.Lake Buena Vista, Dec. 8-11, 1991;[Proceeding of the Ultrasonic Symposium], IEEE, US, vol. 2, Dec. 8, 1991, pp. 1273-1276.

European Office Action issued in European Application No. 12198996.6-1812 dated Jul. 23, 2014.

Korean Notice of Allowance issued in Korean Application No. 10-2014-0050992, dated Jan. 26, 2015, with English translation.

* cited by examiner

ULTRASOUND SYSTEM AND METHOD FOR DETECTING VECTOR INFORMATION USING TRANSMISSION DELAYS

CROSS-REFERENCE TO RELATED APPLICATIONS

The present application claims priority from Korean Patent Application No. 10-2011-0143871 filed on Dec. 27, 2011, the entire subject matter of which is incorporated herein by reference.

TECHNICAL FIELD

The present disclosure generally relates to an ultrasound system, and more particularly an ultrasound system and method for detecting vector information corresponding to motions (i.e., velocities and directions) of a target object.

BACKGROUND

An ultrasound system has become an important and popular diagnostic tool since it has a wide range of applications. Specifically, due to its non-invasive and non-destructive nature, the ultrasound system has been extensively used in the medical profession. Modern high-performance ultrasound systems and techniques are commonly used to produce two-dimensional or three-dimensional ultrasound images of internal features of target objects (e.g., human organs).

The ultrasound system may provide ultrasound images in various modes including a brightness mode image representing reflection coefficients of ultrasound signals reflected from a target object (i.e., ultrasound echoes) with a two-dimensional image, a Doppler mode image representing velocity of a moving target object with spectral Doppler by using a Doppler effect, a color Doppler mode image representing velocity of the moving target object with colors by using the Doppler effect, an elastic image representing mechanical characteristics of tissues before and after applying compression thereto, and the like.

The ultrasound system may transmit the ultrasound signals to the target object and receive the ultrasound echo signals from the target object to form Doppler signals corresponding to a region of interest, which is set on the brightness mode image. The ultrasound system may further form the color Doppler mode image representing the velocities of the moving target object with colors based on the Doppler signals. In particular, the color Doppler image may represent the motions of the target object (e.g., blood flow) with the colors. The color Doppler image may be used to diagnose disease of a blood vessel, a heart and the like. However, it is difficult to represent an accurate motion of the target object (e.g., blood flow) since the respective colors indicated by motion values are a function of the velocity of the target object, which moves forward in a transmission direction of the ultrasound signals and moves backward in the transmission direction of the ultrasound signals.

To cope with the drawback of the color Doppler image, a vector Doppler method capable of obtaining information on velocities and directions of the blood flow has been introduced. A cross beam-based method of the vector Doppler method may acquire velocity magnitude components in at least two different directions, and combine the velocity magnitude components to detect vector information having two-dimensional or three-dimensional direction information and magnitude information.

SUMMARY

An ultrasound system and a method for detecting vector information corresponding to moving velocities and directions of a target object by using transmission delays for at least two focal points are provided.

In one embodiment, there is provided an ultrasound system including: an ultrasound data acquisition unit configured to set at least two focal points in a target object and to form ultrasound data corresponding to the respect two focal points by considering transmission delays to the respective focal points; and a processor configured to form vector information of the target object by using the ultrasound data.

In another embodiment, there is provided a method of detecting vector information including: a) setting at least two focal points in a target object; b) forming ultrasound data corresponding to the respect two focal points by considering transmission delays to the respective focal points; and c) forming vector information of the target object by using the ultrasound data.

DETAILED DESCRIPTION

Hereinafter, embodiments of the present disclosure will be described in detail by referring to the accompanying drawings.

Figure 1:
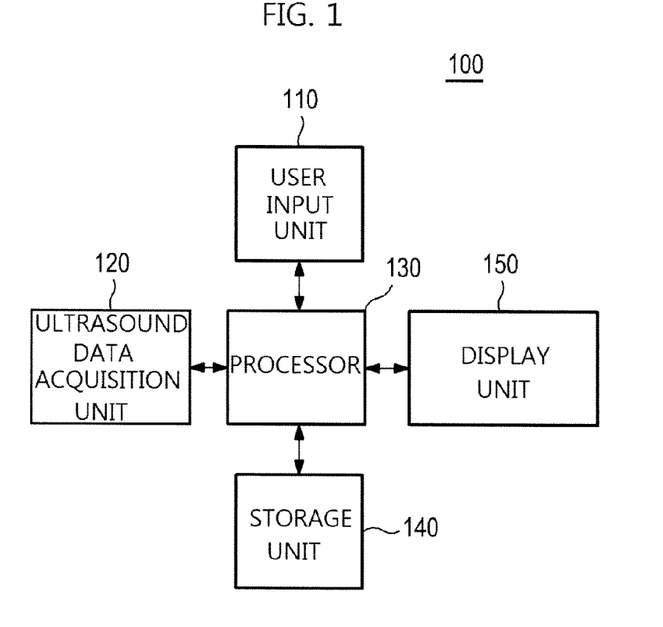
FIG. 1 is a block diagram showing an illustrative embodiment of an ultrasound system.
Figure 2:
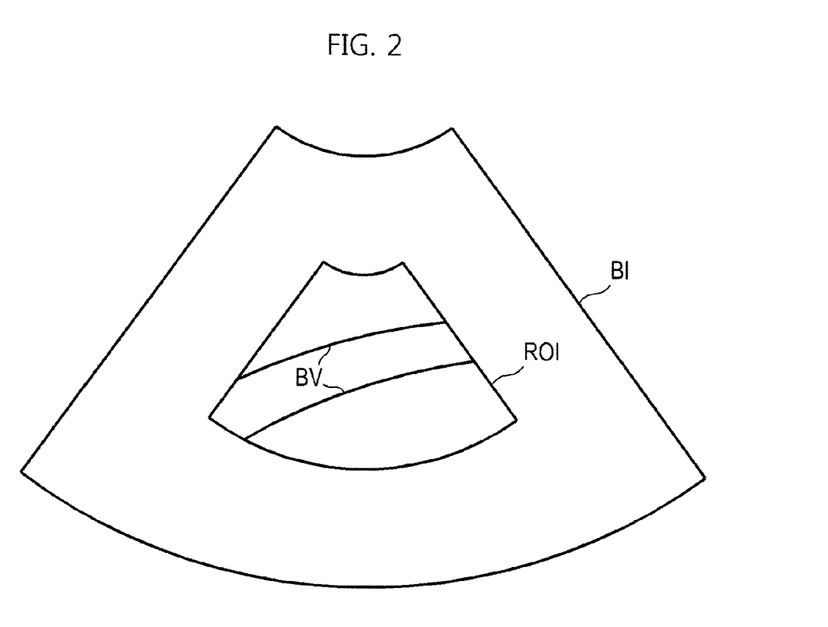
FIG. 2 is an exemplary diagram showing an example of setting a region of interest on a brightness mode image.

FIG. 1 is a block diagram showing an illustrative embodiment of an ultrasound system according to one embodiment of the present disclosure. Referring to FIG. 1, the ultrasound system 100 may include a user input unit 110.

The user input unit 110 may receive input information from a user. In one embodiment, the input information may include information for setting a region of interest. That is, the input information may include information on size and location of the region of interest. However, the input information may not be limited thereto. The region of interest may be a region to detect vector information corresponding to motions (i.e., velocities and directions) of the target object. The user input unit 110 may include at least one of a control panel, a track ball, a touch screen, a mouse, a keyboard and the like.

The ultrasound system 100 may further include an ultrasound data acquisition unit 120. The ultrasound data acquisition unit 120 may be configured to transmit ultrasound signals to an object. The object may include at least one of blood flow, blood flow wall, tissues, heart, and the like as a target object. Also, the ultrasound acquisition unit 120 may be configured to receive ultrasound signal reflected from the object (i.e., ultrasound echo) to acquire ultrasound data for ultrasound imaging.

Figure 3:
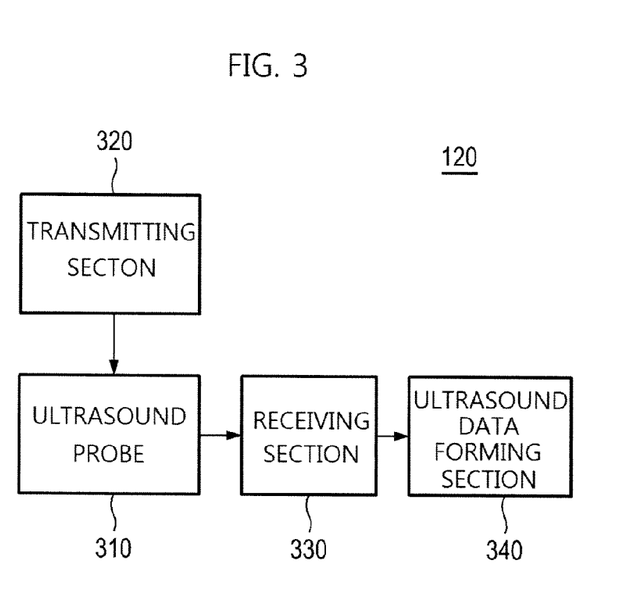
FIG. 3 is a block diagram showing an illustrative embodiment of an ultrasound data acquisition unit.

FIG. 3 is a block diagram showing an illustrative embodiment of the ultrasound data acquisition unit 120 according to one embodiment of the present disclosure. Referring to FIG. 3, the ultrasound data acquisition unit 120 may include an ultrasound probe 310.

The ultrasound probe 310 may include a plurality of transducer elements 311 (see FIGS. 4 and 5), which are operable to reciprocally convert electrical signals and ultrasound signals. The ultrasound probe 310 is configured to transmit ultrasound signals to the object and receive ultrasound echoes reflected from the object to thereby output receive signals of electrical signals, which may be analog signals. The ultrasound probe 310 may include at least one of a convex probe, a linear probe and the like.

The ultrasound data acquisition 120 may further include a transmitting section 320. The transmitting section 320 may be configured to control transmission of the ultrasound signals. Further, the transmitting section 320 is configured to generate transmission pulses and apply delays to the transmission pulses by considering distances from the respective transducer elements 311 to a focal point, thereby forming transmission signals. The transmission signals may be transferred to the transducer elements 311 of the ultrasound probe 310 for excitation. The transmitting section 320 may include a transmission pulse generator (not denoted), a memory to store information on transmission delays (not denoted), a transmission beam former (not denoted) and the like.

In one embodiment, the transmitting section 320 may be configured to form transmission signals to acquire a brightness mode (B-mode) image by considering distances from the respective transducer elements 311 to a focal point. Herein, the transmission signals will be referred to as B-mode transmission signals. The ultrasound probe 310 may transmit ultrasound signals to the object in response to the B-mode transmit signals and receive ultrasound echoes reflected from the object, thereby outputting receive signals (hereinafter referred to as B-mode receive signals).

Also, the transmitting section 320 may be configured to form transmission signals corresponding to an ensemble number to acquire a Doppler mode image, wherein the transmission signals will be referred to as Doppler mode transmission signals. The ensemble number represents the number of times for transmitting and receiving the ultrasound signals to and from the object. The ultrasound probe 310 may transmit ultrasound signals to the object in response to the Doppler mode transmission signals and receive ultrasound echoes reflected from the object, thereby outputting receive signals (hereinafter referred to as Doppler mode receive signals).

Figure 4:
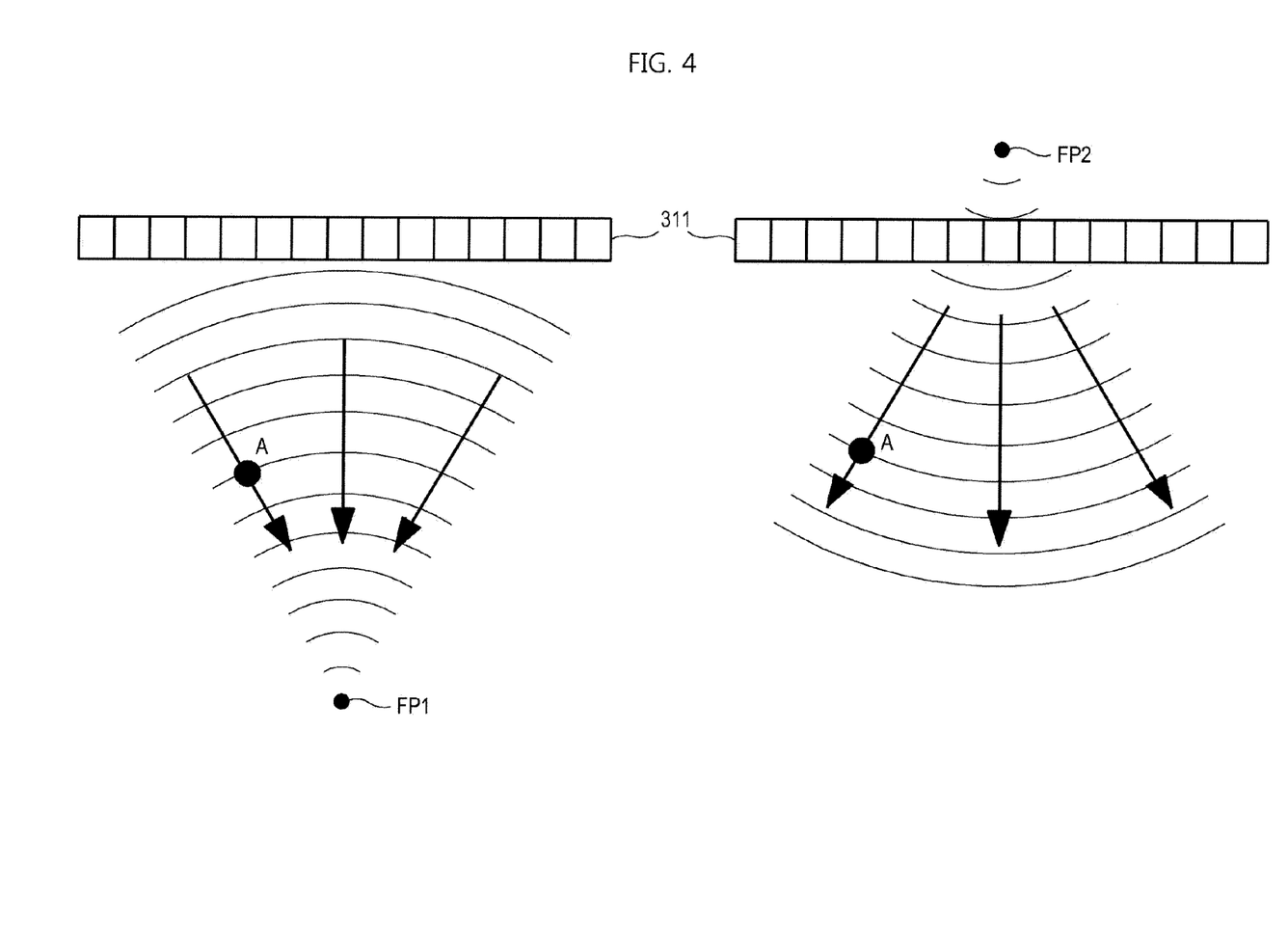
FIG. 4 is an exemplary diagram showing an example of setting focal points according to one embodiment of the present disclosure.

More particularly, the transmitting section 320 may be configured to set at least two focal points. For example, the transmitting section 320 is configured to set a first focal point FP1 in a transmission direction of the ultrasound signals from the transducer elements 311, and to set a second focal point FP2 in an opposite transmission direction of the ultrasound signals from the transducer elements, as shown in FIG. 4. The transmitting section 320 may be configured to compute first transmission delays corresponding to the first focal point FP1 by considering distances between the respect transducer elements and the first focal point FP1, as shown in FIG. 4. The transmitting section 320 may also be configured to form first Doppler-mode transmission signals corresponding to the ensemble number by applying the first transmission delays to the transmission pulses. The ultrasound probe 310 may be configured to transmit ultrasound signals to the object in response to the first Doppler-mode transmission signals and receive ultrasound echoes reflected from the target object, thereby outputting first Doppler-mode receive signals. Further, the transmitting section 320 may be configured to compute second transmission delays corresponding to the second focal point FP2 by considering distances between the respect transducer elements and the second focal point FP2, as shown in FIG. 4. The transmitting section 320 may further be configured to form second Doppler-mode transmission signals corresponding to the ensemble number by applying the second transmission delays to the transmission pulses. The ultrasound probe 310 may be configured to transmit ultrasound signals to the object in response to the second Doppler-mode transmission signals and receive ultrasound echoes reflected from the target object, thereby outputting second Doppler-mode receive signals.

Although it is described in the above embodiment that two focal points are set with respect to the transducer elements 311, it should be noted that the number and location of the focal point may not be limited thereto. The focal points may be set variously depending on the need.

Referring to FIG. 3 again, the ultrasound data acquisition unit 120 may further include a receiving section 330. The receiving section 330 may be configured to perform analog-to-digital conversion upon the receive signals, which are provided from the ultrasound probe 310, to form digital signals. Further, the receiving section 330 may be configured to perform reception beam focusing upon the digital signals by considering the distances between the respective transducer elements 311 and the focal points, thereby forming receive-focused signals. The receive-focusing may be performed through well-known methods. As such, a detailed description thereof will be omitted herein. The receiving section 330 may include a receive signal amplifier (not denoted), an analog-to-digital converter (not denoted), a memory (not denoted) to store information on receive delays, a reception beam former (not denoted) and the like.

In one embodiment, the receiving section 330 is configured to perform analog-to-digital conversion upon the B-mode receive signals to form digital signals (hereinafter referred to as B-mode digital signals). The receiving section 330 is configured to perform reception beam forming upon the B-mode digital signals to form B-mode receive-focused signals.

Further, the receiving section 330 is configured to perform analog-to-digital conversion upon the Doppler mode receive signals to form digital signals (hereinafter referred to as Doppler mode digital signals). The receiving section 330 is configured to perform reception beam forming upon the Doppler mode digital signals to form Doppler mode receive-focused signals.

For example, the receiving section 330 is configured to digitize the Doppler mode receive signals, which are provided from the ultrasound probe 310, to thereby form first Doppler mode digital signals. The receiving section 330 is configured to perform reception beam forming upon the first Doppler mode digital signals by considering distances between the respective transducer elements 311 and a first focal point FP1 to form first Doppler mode receive-focused signals. Also, the receiving section 330 is configured to digitize the Doppler mode receive signals, which are provided from the ultrasound probe 310, to thereby form second Doppler mode digital signals. The receiving section 330 is configured to perform reception beam forming upon the second Doppler mode digital signals by considering distances between the respective transducer elements 311 and a second focal point FP2 to form second Doppler mode receive-focused signals.

The ultrasound acquisition unit 120 may further include an ultrasound data forming section 340. The ultrasound data forming section 340 is configured to form ultrasound data for ultrasound imaging by using the receive-focused signals, which are provided from the receiving section 330. Further, the ultrasound data forming section 340 is configured to perform various signal processing necessary for forming the ultrasound image, such as gain control, etc., upon the receive-focused signals.

In one embodiment, the ultrasound data acquisition unit 120 may be configured to form ultrasound data for B-mode ultrasound imaging (hereinafter referred to B-mode ultrasound data) by using the B-mode receive-focused signals, which are provided from the receiving section 330. The B-mode ultrasound data may include radio frequency (RF) data, but may not be limited thereto.

Further, the ultrasound data acquisition unit 120 may be configured to form ultrasound data for Doppler mode ultrasound imaging (hereinafter referred to Doppler mode ultrasound data) by using the Doppler mode receive-focused signals, which are provided from the receiving section 330. The Doppler mode ultrasound data may include radio in-phase/quadrature (IQ) data, but may not be limited thereto.

For example, the ultrasound data forming section 340 is configured to form first Doppler mode ultrasound data by using the first Doppler mode receive-focused signals, which are provided from the receiving section 330. Further, the ultrasound data forming section 340 is configured to form second Doppler mode ultrasound data by using the second Doppler mode receive-focused signals, which are provided from the receiving section 330.

Referring to FIG. 1 again, the ultrasound system 100 may further include a processor 130. The processor 130 is coupled to the user input unit 110 and the ultrasound data acquisition unit 120. The processor 130 may include at least one of a central processing unit, a microprocessor, a graphic processing unit and the like.

Figure 5:
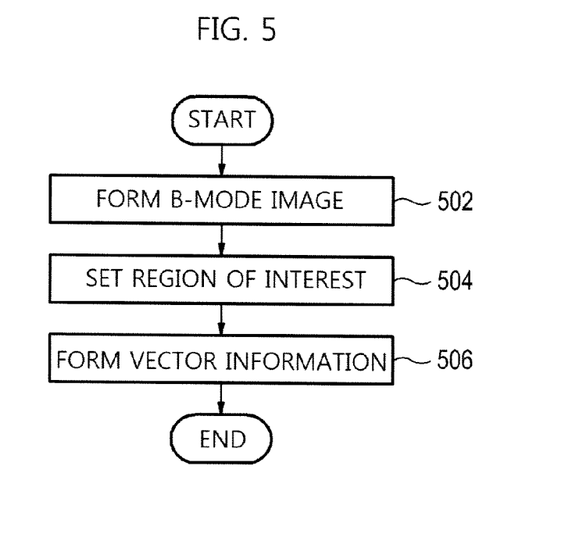
FIG. 5 is a flowchart showing a procedure of detecting vector information using transmission delays according to one embodiment of the present disclosure.

FIG. 5 is a flowchart showing a process of detecting vector information by using transmission delays according to one embodiment of the present disclosure. Referring to FIG. 5, the processor 130 may be configured to form a B-mode image by using the B-mode ultrasound data, which are provided from the ultrasound data acquisition unit 120, at S502. The B-mode image may be displayed on a display unit 150.

The processor 130 is configured to set a region of interest on the B-mode ultrasound image BI based on the input information provided from the user input unit 110 at S504. The ultrasound data acquisition unit 120 is configured to set at least two focal points based on the region of interest. The ultrasound data acquisition unit 120 is configured to transmit ultrasound signals to an object by considering the focal points and receive ultrasound echoes reflected from the object to thereby acquire Doppler mode ultrasound data corresponding to the at least two focal points.

The processor 130 is configured to form vector information by using the Doppler mode ultrasound data, which are provided from the ultrasound data acquisition unit 120, at S1506. That is, the processor 130 is configured to form the vector information corresponding to motion of the target object (i.e., velocities and directions) by using the Doppler mode ultrasound data.

Generally, when the transmission direction of the ultrasound signals is equal to the reception direction of the ultrasound echo signals and a Doppler angle is θ, the following relationship may be established:

$$X\cos\theta = \frac{C_0 f_d}{2 f_0} \quad (1)$$

In equation (1), X represents a reflector velocity (i.e., velocity of target object), $C_0$ represents a sound speed in the object, $f_d$ represents a Doppler shift frequency, and $f_0$ represents a frequency of an ultrasound signal.

The Doppler shift frequency $f_d$ may be calculated by a difference between a frequency of the ultrasound signals (i.e., transmission beam) and a frequency of the ultrasound echoes (i.e., reception beam). Also, the velocity component $X \cos \theta$ projected to the transmission direction may be calculated by the equation (1).

In the meantime, when the transmission direction of the ultrasound signals (i.e., transmission beam) is different to the reception direction of the ultrasound echoes (i.e., reception beam), the following relationship may be established:

$$X\cos\theta_T + X\cos\theta_R = \frac{C_0 f_d}{f_0} \quad (2)$$

In equation (2), $\theta_T$ represents an angle between a transmission direction of the ultrasound signals (i.e., transmission beam) and a flow direction of the blood flow, and $\theta_R$ represents an angle between a reception direction of the ultrasound echo signals (i.e., reception beam) and a flow direction of the blood flow.

Figure 6:
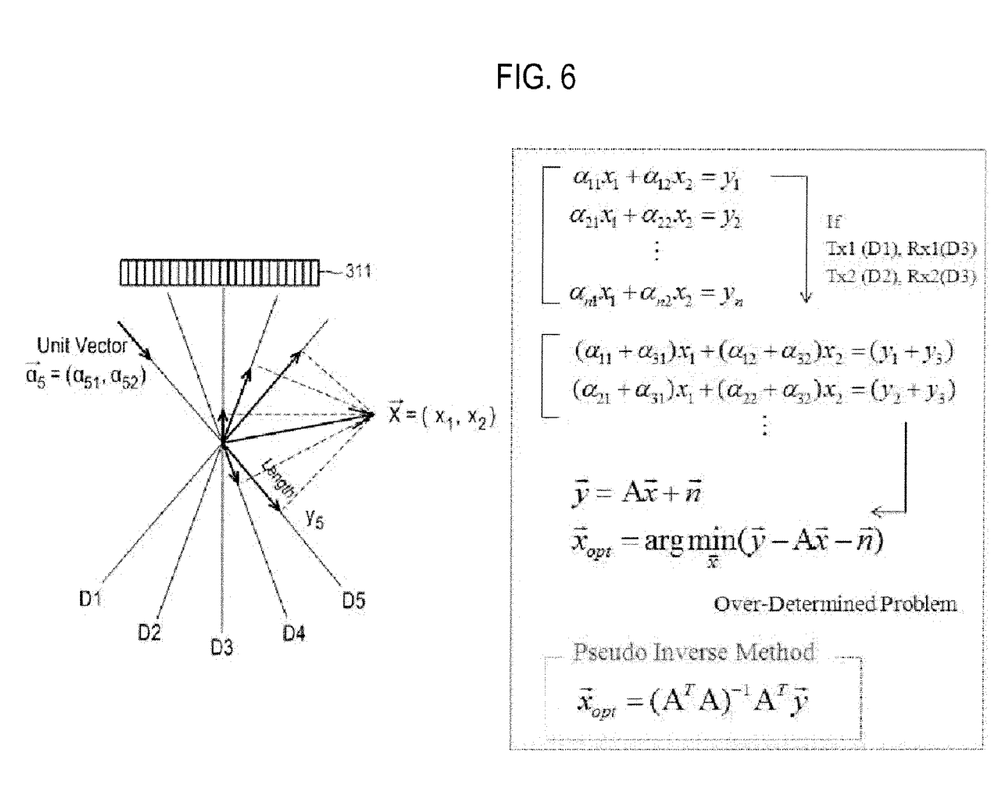
FIG. 6 is a schematic diagram showing an example of the transmission directions, the reception directions, the vector information and an over-determined problem.

FIG. 6 is a schematic diagram showing an example of the transmission directions, the reception directions, the vector information and an over-determined problem. Referring to FIG. 16, when the ultrasound signals (i.e., transmission beam) are transmitted in a first direction D1 and the ultrasound echo signals (i.e., reception beam) are received in the first direction D1, the following relationship may be established:

$$\vec{a}_1 \times \vec{X} \times \alpha_{11} x_1 + \alpha_{12} x_2 = y_1 = X \cos\theta \quad (3)$$

In equation 3, $\vec{a}_1 = (\alpha_{11}, \alpha_{12})$ indicative of a unit vector in the first direction D1, $\vec{X} = (x_1, x_2)$ indicative of variables, and $y_1$ is calculated by equation (1).

In the meantime, when the ultrasound signals (i.e., transmission beam) are transmitted in a second direction D2 and the ultrasound echo signals (i.e., reception beam) are received in a third direction D3, the following relationship may be established:

$$(\alpha_{21}+\alpha_{31})x_1+(\alpha_{22}+\alpha_{32})x_2=(y_2+y_3)=X\cos\theta_2+X\cos\theta_3 \quad (4)$$

Equations (3) and (4) are established under the assumption of a two-dimensional environment. However, equations (3) and (4) may be expanded to a three-dimensional environment. That is, when expanding equations (3) and (4) to the three-dimensional environment, the following relationship may be established:

$$\alpha_{11}x_1+\alpha_{12}x_2+\alpha_{13}x_3=y \quad (5)$$

In the case of the two-dimensional environment (i.e., two-dimensional vector), at least two equations are required to calculate the variables $x_1$ and $x_2$. For example, when the ultrasound signals (i.e., transmission beam) are transmitted in the third direction D3 and the ultrasound echo signals (i.e., reception beam) are received in the second direction D2 and a fourth direction D4 as shown in FIG. 16, the following equations may be established:

$$(\alpha_{31}+\alpha_{21})x_1+(\alpha_{32}+\alpha_{22})x_2=(y_3+y_2) \quad (5)$$

$$(\alpha_{31}+\alpha_{41})x_1+(\alpha_{32}+\alpha_{42})x_2=(y_3+y_4) \quad (6)$$

The vector $\vec{X}=(x_1, x_2)$ may be calculated by the two equations (6).

In the meantime, when the reception beam-forming is performed in at least two angles (i.e., at least two reception directions), at least two equations may be obtained and represented as the over-determined problem, as shown in FIG. 6. The over-determined problem is well known in the art. Thus, it has not been described in detail so as not to unnecessarily obscure the present disclosure. The over-determined problem may be solved by a pseudo inverse method, a weighted least square method and the like based on noise characteristics added to the Doppler shift frequency. That is, M×N equations may be obtained by M transmission directions and the reception beam-forming of N reception directions at every transmission.

For example, the processor 130 is configured to detect vector information by using the first Doppler mode ultrasound data corresponding to the first focal point and the second Doppler mode ultrasound data corresponding to the second focal point for an arbitrary region A denoted in FIG. 4, based on the above equations.

Alternatively, the processor 130 may be configured to form a Doppler mode image corresponding to the region of interest by using the vector information. The Doppler mode image may include a vector Doppler image or a color Doppler image. The vector Doppler image may be formed through well-known methods. As such, detailed description thereof will be omitted herein.

Referring to FIG. 1 again, the ultrasound system 100 may further include a storage unit 140. The storage unit 140 may be configured to store the ultrasound data (i.e., B-mode ultrasound data and Doppler mode ultrasound data), which are acquired by the ultrasound data acquisition unit 120. Further, the storage unit 140 may store the vector information. Also, the storage unit 140 may store the B-mode image and the Doppler mode image, which are formed by the processor 130.

The ultrasound system 100 may further include a display unit 150. The display unit 150 may display the B-mode image formed by the processor 130. Further, the display unit 150 may display the Doppler mode image formed by the processor 130.

Although embodiments have been described with reference to a number of illustrative embodiments thereof, it should be understood that numerous other modifications and embodiments can be devised by those skilled in the art that will fall within the spirit and scope of the principles of this disclosure. More particularly, numerous variations and modifications are possible in the component parts and/or arrangements within the scope of the disclosure, the drawings and the appended claims. In addition to variations and modifications in the component parts and/or arrangements, alternative uses will also be apparent to those skilled in the art.

What is claimed is:

1. A medical diagnostic ultrasound system, comprising:
an ultrasound data acquisition unit configured to set at least two focal points and form ultrasound data corresponding to the respective at least two focal points by performing a beam forming upon a plurality of echo signals corresponding to a plurality of signals transmitted to the respective at least two focal points, wherein the beam forming is performed by considering transmission delays to the respective at least two focal points and the transmission delays are determined to set the at least two focal points on different locations respectively; and
a processor configured to form vector information of a target object by using the ultrasound data,
wherein the plurality of echo signals are generated by being reflected from a target object and transmitted to the respective at least two focal points, and the ultrasound data comprise vector information including different velocities and directions of the target object, and
wherein the ultrasound data acquisition unit is configured to:
set transmission delays corresponding to the respective at least two focal points;
form transmission pulses corresponding to the respective at least two focal points by considering the transmission delays;
transmit ultrasound a plurality of signals into the target object in response to the transmission pulses and receive ultrasound echoes to form a plurality of receive signals;
perform analog-to-digital conversion upon the plurality of receive signals to form a plurality of digital signals;
perform reception beam forming upon the plurality of digital signals to form a plurality of receive-focused signals; and
form ultrasound data corresponding to the respective at least two focal points by using the plurality of receive-focused signals.

2. A medical diagnostic method of detecting vector information, comprising:
a) setting at least two focal points;
b) forming ultrasound data corresponding to the respective at least two focal points by performing a beam forming upon a plurality of echo signals corresponding to a plurality of signals transmitted to the respective at least two focal points, wherein the beam forming is performed by considering transmission delays to the respective at least two focal points and the transmission delays are determined to set the at least two focal points on different locations respectively;
c) forming vector information of a target object by using the ultrasound data,
wherein the plurality of echo signals are generated by being reflected from a target object and transmitted to the respective at least two focal points, and the ultrasound data comprise vector information including different velocities and directions of the target object, and
wherein the forming b) includes:
setting transmission delays corresponding to the respective at least two focal points;
forming transmission pulses corresponding to the respective at least two focal points by considering the transmission delays;
transmitting a plurality of ultrasound signals into the target object in response to the transmission pulses and receive ultrasound echoes to form a plurality of receive signals;
performing analog-to-digital conversion upon the plurality of receive signals to form a plurality of digital signals;

performing reception beam forming upon the plurality of digital signals to form a plurality of receive-focused signals; and forming ultrasound data corresponding to the respective at least two focal points by using the plurality of receive-focused signals.

\* \* \* \* \*